(12) United States Patent
Gebauer et al.

(10) Patent No.: US 12,084,645 B2
(45) Date of Patent: Sep. 10, 2024

(54) SUPPORT VESSELS FOR SINGLE USE BIOREACTORS AND MIXERS

(71) Applicant: CYTIVA SWEDEN AB, Uppsala (SE)

(72) Inventors: Klaus Gebauer, Uppsala (SE); Thomas Erik Arctaedius, Uppsala (SE); Patrick Jonsson, Uppsala (SE); Andreas Marcstrom, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 795 days.

(21) Appl. No.: 16/301,150

(22) PCT Filed: May 11, 2017

(86) PCT No.: PCT/EP2017/061276
§ 371 (c)(1),
(2) Date: Nov. 13, 2018

(87) PCT Pub. No.: WO2017/194652
PCT Pub. Date: Nov. 16, 2017

(65) Prior Publication Data
US 2019/0194589 A1 Jun. 27, 2019

Related U.S. Application Data

(60) Provisional application No. 62/336,301, filed on May 13, 2016.

(51) Int. Cl.
*C12M 3/00* (2006.01)
*C12M 1/00* (2006.01)

(52) U.S. Cl.
CPC ............ *C12M 23/40* (2013.01); *C12M 23/14* (2013.01); *C12M 23/26* (2013.01); *C12M 23/28* (2013.01); *C12M 23/48* (2013.01)

(58) Field of Classification Search
CPC ...... C12M 23/14; C12M 23/26; C12M 23/28; C12M 23/40; C12M 23/48; C12M 41/18; C12M 41/22; C12M 23/44; A61K 38/00
See application file for complete search history.

(56) References Cited

U.S. PATENT DOCUMENTS

| 4,197,689 A | 4/1980 | Demuth |
| 4,282,861 A * | 8/1981 | Roark ................ F24D 17/0021 165/169 |

(Continued)

FOREIGN PATENT DOCUMENTS

| CN | 1185554 A | 6/1998 |
| CN | 2612674 | 4/2004 |

(Continued)

OTHER PUBLICATIONS

International Search Report dated Aug. 9, 2017 from corresponding PCT Patent Application No. PCT/EP2017/061276.

(Continued)

*Primary Examiner* — Nathan A Bowers
(74) *Attorney, Agent, or Firm* — Grogan, Tuccillo & Vanderleeden LLP (57) ABSTRACT

The invention discloses a hollow profile wall segment (1) for a bioreactor or mixer support vessel (2;2a;2b), comprising a base profile (3) with two parallel wide sides (4,5), two narrow sides (6,7) and at least one heat exchange channel (8) extending in a longitudinal direction of the base profile through an interior space (9) in the base profile, wherein the hollow profile wall segment is adapted to be joined with similar hollow profile wall segments to form a side wall (12) of a bioreactor or mixer support vessel (2) and wherein each narrow side comprises at least one coupling member (10, (Continued)

11;11a;150) capable of securing the hollow profile wall segment side by side with similar hollow profile wall segments.

32 Claims, 12 Drawing Sheets

(56) References Cited

U.S. PATENT DOCUMENTS

| | | | | |
|---|---|---|---|---|
| 5,923,819 A | * | 7/1999 | Ross | B29C 65/58 |
| | | | | 392/441 |
| 2005/0274499 A1 | * | 12/2005 | Rule | F28D 1/06 |
| | | | | 165/129 |
| 2013/0089925 A1 | * | 4/2013 | Damren | F28F 9/0131 |
| | | | | 435/303.1 |
| 2014/0318067 A1 | * | 10/2014 | Richardson | E04G 17/06 |
| | | | | 52/428 |
| 2015/0029815 A1 | | 1/2015 | Gebauer et al. | |
| 2015/0299641 A1 | * | 10/2015 | Galliher | F16L 11/04 |
| | | | | 383/105 |

FOREIGN PATENT DOCUMENTS

| | | |
|---|---|---|
| CN | 202089981 | 12/2011 |
| CN | 104168993 A | 11/2014 |
| CN | 104903674 A | 9/2015 |

OTHER PUBLICATIONS

Corresponding Chinese Patent Application No. 201780029291.9 Office Action dated Jul. 28, 2021.

* cited by examiner

SUPPORT VESSELS FOR SINGLE USE BIOREACTORS AND MIXERS

CROSS-REFERENCE TO RELATED APPLICATIONS

This application claims the benefit of PCT International Application No. PCT/EP2017/061276, having an International Filing Date of May 11, 2017, which, in turn, claims priority to, and the benefit of, U.S. Provisional Patent Application No. 62/336,301, filed on May 13, 2016, both of which are herein incorporated by reference in their entirety.

TECHNICAL FIELD OF THE INVENTION

The present invention relates to single use bioreactors and mixers for use in bioprocess applications and in particular to support vessels for such single use bioreactors and mixers. The invention also relates to hollow profile segments and sections that can be assembled to form side walls of support vessels.

BACKGROUND OF THE INVENTION

In the bioprocess field, bioreactors and mixers are typically designed as jacketed allowing for heat transfer to achieve temperature control for process liquids such as cell cultures, cell culture media or buffers by either cooling or heating a heat exchange (HX) fluid circulating through the jacket. This design is applied also to single-use applications where the internal of the vessel is fitted with a single use closed plastic bag holding the liquid. The cost of the re-usable jacketed tank used in single-use applications, however, is equally expensive as the equivalent equipment in traditional (non-single use) processes as the design principles and manufacturing technologies for building the jacketed applied today are identical. Stainless steel constructions are laminated by extensive welding operations.

Accordingly there is a need for a more cost efficient design of jacketed support vessels for single use flexible bags, in order to fully exploit the simplicity and cost reductions enabled by single-use technology.

SUMMARY OF THE INVENTION

Inexpensive hollow (e.g. extruded) extruded profiles can be used to produce elongated hollow structures that serve as conduits for the heat exchange fluid. By arranging multiple hollow profiles adjacent to each other, a wall structure can be formed that resembles a conventional jacketed wall of a vessel.

The alternative design can take advantage of the fact that the fluid is no longer in direct contact with the vessel wall when employing single-use bags. Materials and surface structures can thereby be different compared to traditional processing equipment.

One aspect of the invention is to provide a hollow profile wall segment allowing the cost-effective construction of a jacketed bioreactor or mixer support vessel. This is achieved with a wall segment comprising a base profile with two parallel wide sides, two narrow sides and at least one heat exchange channel which extends in a longitudinal direction of the base profile through an interior space in the profile. The wall segment is adapted to be joined with similar wall segments to form a side wall of a bioreactor or mixer support vessel and each narrow side comprises at least one coupling member capable of securing the wall segment side by side with similar wall segments.

One advantage is that the manufacturing cost of the profiles is low. Further advantages are that they can easily be assembled to form jacketed vessel walls and that it is possible to provide a wide range of different flow path patterns.

A second aspect of the invention is a side wall of a bioreactor or mixer support vessel, which comprises a plurality of hollow profile wall segments, each comprising a base profile with two parallel wide sides, two narrow sides and at least one heat exchange channel extending in a longitudinal direction of the base profile through an interior space in the base profile, where the wall segments are joined side by side.

A third aspect of the invention is to provide a bioreactor or mixer support vessel comprising a side wall as discussed above, a bottom wall and top and bottom distribution manifolds, fluidically connecting a plurality of the heat exchange channels with an inlet and an outlet.

A fourth aspect of the invention is to provide a bioreactor or mixer comprising a flexible bag mounted in a support vessel as discussed above.

A fifth aspect of the invention is to provide hollow profile wall section for a cylindrical bioreactor or mixer support vessel, which comprises a base tubular section with an inner surface, an outer surface and a plurality of heat exchange channels extending in an axial direction through the base tubular section, wherein the wall section is arranged to be stacked with similar wall sections.

A sixth aspect of the invention is to provide a cylindrical side wall of a bioreactor or mixer support vessel, comprising a plurality of stacked hollow profile wall sections as discussed above, wherein the heat exchange channels of the stacked sections are in register with each other.

A seventh aspect of the invention is to provide a bioreactor or mixer support vessel comprising the cylindrical side wall as discussed above, a bottom wall and top and bottom distribution manifolds, fluidically connecting a plurality of the heat exchange channels with an inlet and an outlet.

Further suitable embodiments of the invention are described in the dependent claims.

DEFINITIONS

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about" Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

As used herein to describe the present invention, directional terms such as "up", "down", "top", "bottom", "vertical", "horizontal", as well as any other directional terms, refer to those directions of a bioreactor or mixer as used in the normal operational position.

DETAILED DESCRIPTION OF EMBODIMENTS

Figure 12:
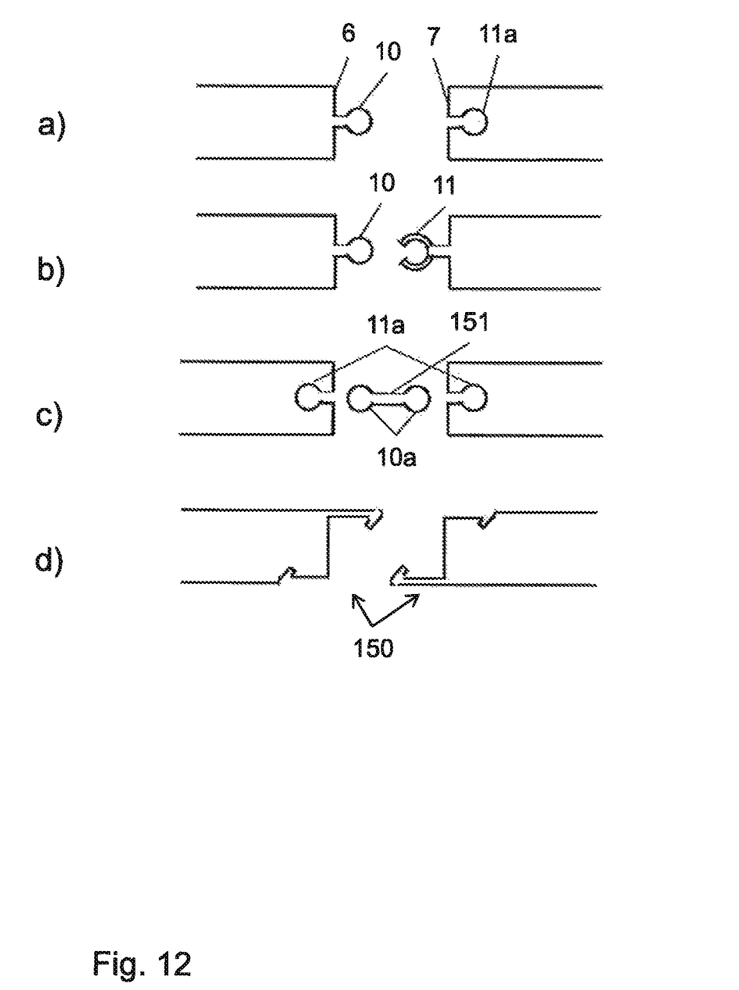
FIG. 12 shows different varieties (cross sections) of locking/coupling elements for segments of the invention. a) Protruding male element and recessed female element, b) Protruding male and female elements, c) Recessed female elements on segments and male elements on separate coupling profile, d) Genderless elements.

In one aspect, illustrated by FIGS. 1-4, the present invention discloses an elongated hollow profile wall segment 1 for a bioreactor or mixer support vessel 2;2*a*;2*b*. The wall segment comprises a base profile 3 with two parallel wide sides 4,5 two narrow sides 6,7 and at least one heat exchange channel 8 that extends in a longitudinal direction of the base profile through an interior space 9 in the base profile. The length ratio W/N of the wide sides to the narrow sides may e.g. be at least about 5, such as at least about 10, and/or the ratio of the segment length L to the wide side length W may e.g. be at least about 5, such as at least about 10. The base profile may have a substantially constant cross section geometry along a longitudinal axis 13, e.g. over at least 80% or at least 90% of the length of the profile or over the entire length of the profile. The wall segment is further adapted to be joined with similar wall segments to form a side wall 12 of a bioreactor or mixer support vessel 2;2*a*;2*b* and each narrow side comprises at least one coupling member 10,11 capable of securing the wall segment side by side with similar wall segments. The segments can comprise along their sides a fixation functionality or coupling member such as recesses, tracks and protrusions. These can be employed to lock the elements against each other, for example by longitudinally sliding the elements into each other or by bending the elements from an attachment to a locking angle. A first narrow side 6 may e.g. comprise a male coupling member 10 and a second narrow side 7 may comprise a female coupling member 11;11*a*. The coupling members may e.g. comprise a recess, a track and/or a protrusion. If both coupling members are protruding from the narrow side (as in FIGS. 1 and 12 *b*), the joints may have some angular flexibility, which facilitates the joining. In this case it may be desirable to apply seal strips (not shown) over the joint to provide a smooth surface. If one coupling member is protruding and the other recessed in the narrow side (as in FIGS. 3 and 12 *a*), a less flexible joint will be formed and seal strips may not be needed, particularly if the two narrow sides are in abutment with each other. This will also be the case for the embodiments shown in FIG. 12 *c*), where both segments have recessed female coupling elements 11*a* joined together by a separate coupling profile 151 with two male coupling elements 10*a* arranged to engage elements 11*a* by longitudinally sliding the male coupling elements 10*a* into the female coupling elements 11*a*. Alternatively, the two narrow sides may each comprise a genderless or hermaphroditic coupling member 150. The wall segment may be generally shaped as a sector of a circular tubular cylinder (i.e. with a cross section corresponding to a circular arc, with the segment having a concave side 4 and a convex side 5), which allows for assembly of a circular cylindrical side wall 12;112 with the concave sides 4 forming the inside 18 of the wall and the convex sides 5 forming the outside 19 of the wall. Alternatively, the wall segment may have a generally rectangular shape, with straight sides. This allows for assembly of vessels of polygonal prism shape, such as a right polygonal prism. With a large number of rectangular wall elements, e.g. eight or higher, such a polygonal prism shape may approximate a circular cylindrical shape. In this case, vessel walls of different diameters may be assembled using a single type of wall segment.

In some embodiments, the hollow profile wall segment is an extruded profile, such as an extruded metal profile or an extruded plastic profile. Aluminium and aluminium alloys are commonly used in extruded profiles and the hollow profile wall segment can suitably be an extruded aluminium or aluminium alloy profile. Alternatively, the hollow profile wall segment may be manufactured from sheet metal, such as stainless steel sheet, e.g. by roll forming and (automated) welding. Metals, such as aluminium or aluminium alloys, have generally high thermal conductivities which is beneficial for the heat transfer efficiency.

In certain embodiments, the at least one heat exchange channel 8 contains one or more internal baffle elements (not shown). These promote turbulence and thereby achieve good heat transfer from the HX flow path, The baffle elements can e.g. be tortuous inserts acting as static mixer elements, e.g. inserts having a helical structure. Examples of such tortuous inserts are shown in e.g. U.S. Pat. No 3,286,992 and U.S. Pat. No. 3,635,444, which are hereby incorporated by reference in their entireties. The baffle elements can however also be bulk fillers (particles), elongated structures, Raschig rings etc.

Figure 1:
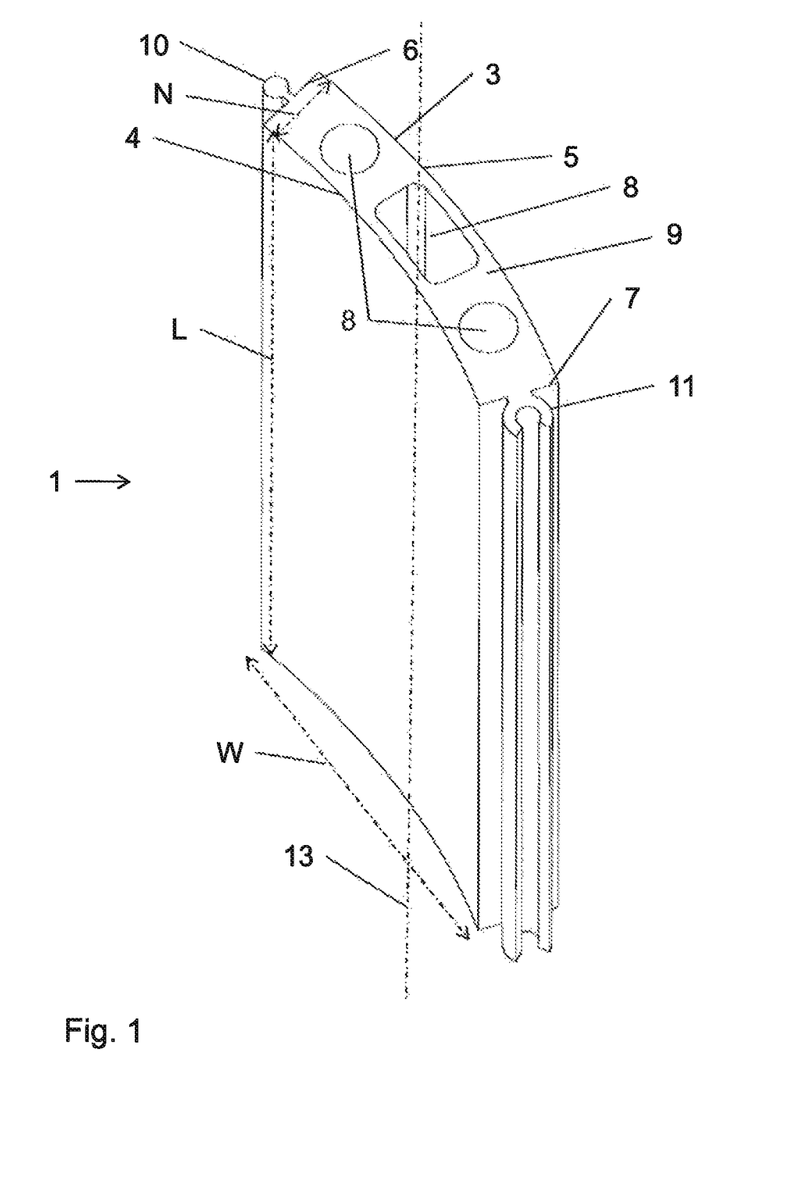
FIG. 1 shows a hollow profile segment (module) of the invention with locking/coupling elements at both sides. Different alternatives for hollow internal conduits/heat exchange channels for guiding a FIX fluid are shown, here cylindrical and rectangular.
Figure 2:
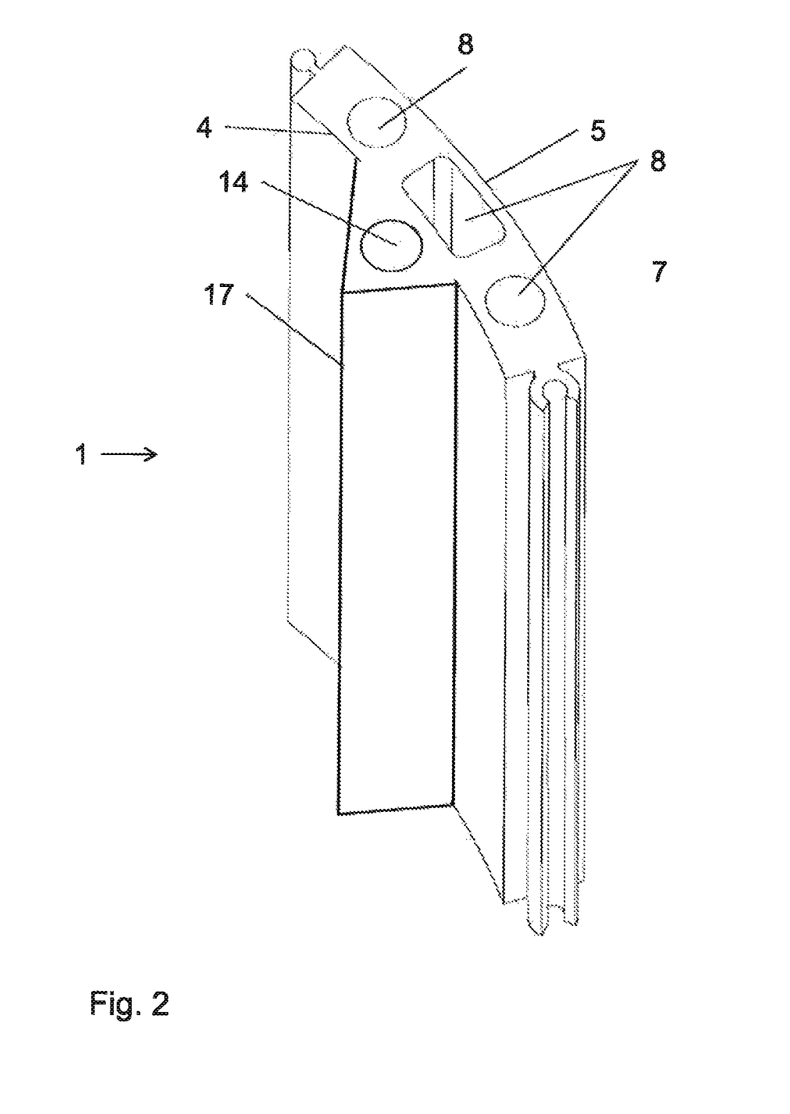
FIG. 2 shows a segment of the invention with a triangular baffle on the side facing inwards.
Figure 3:
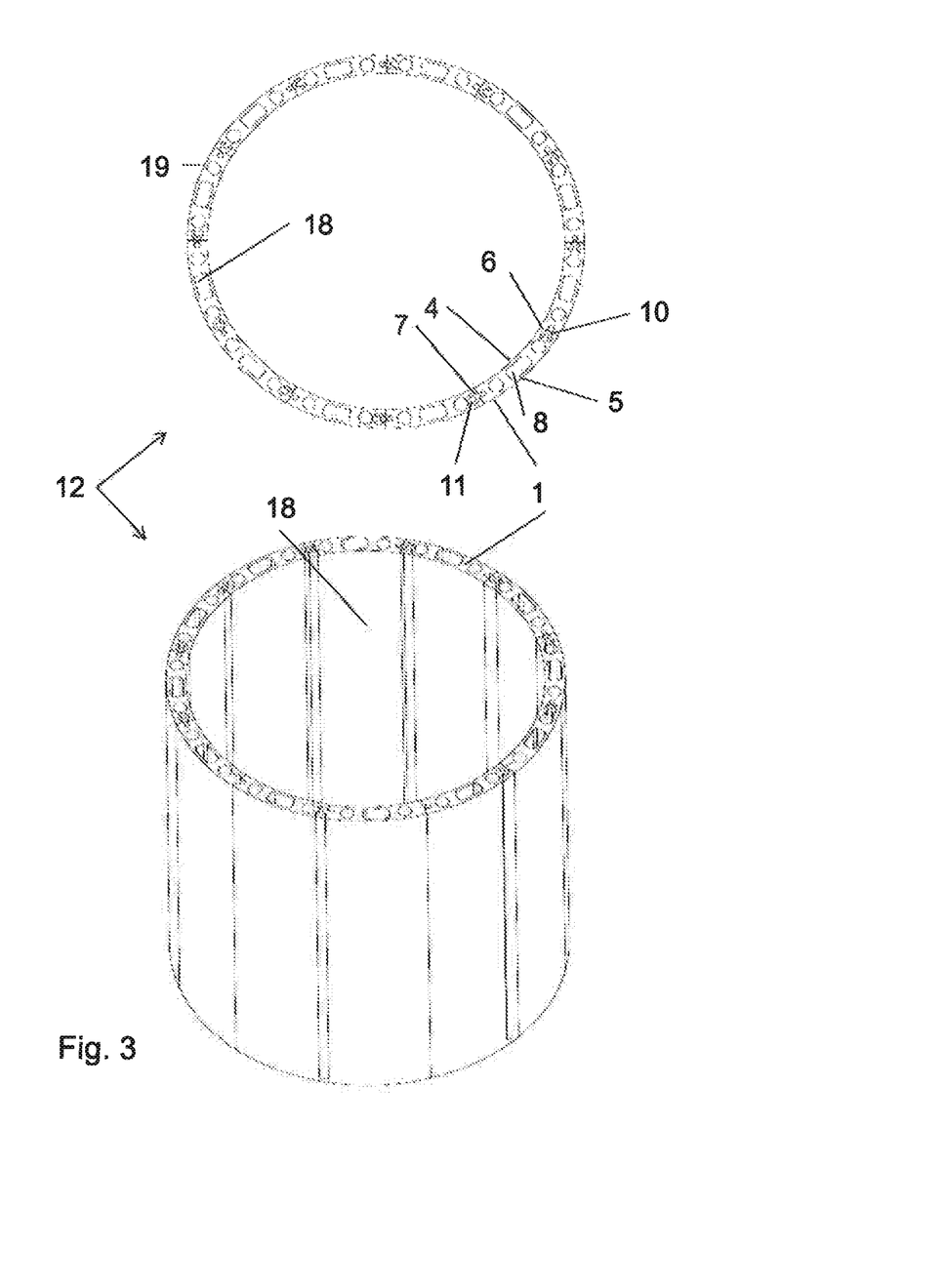
FIG. 3 shows hollow profile segments (modules) forming a rigid cylindrical vessel side wall comprising heat exchange (HX) functionality.
Figure 4:
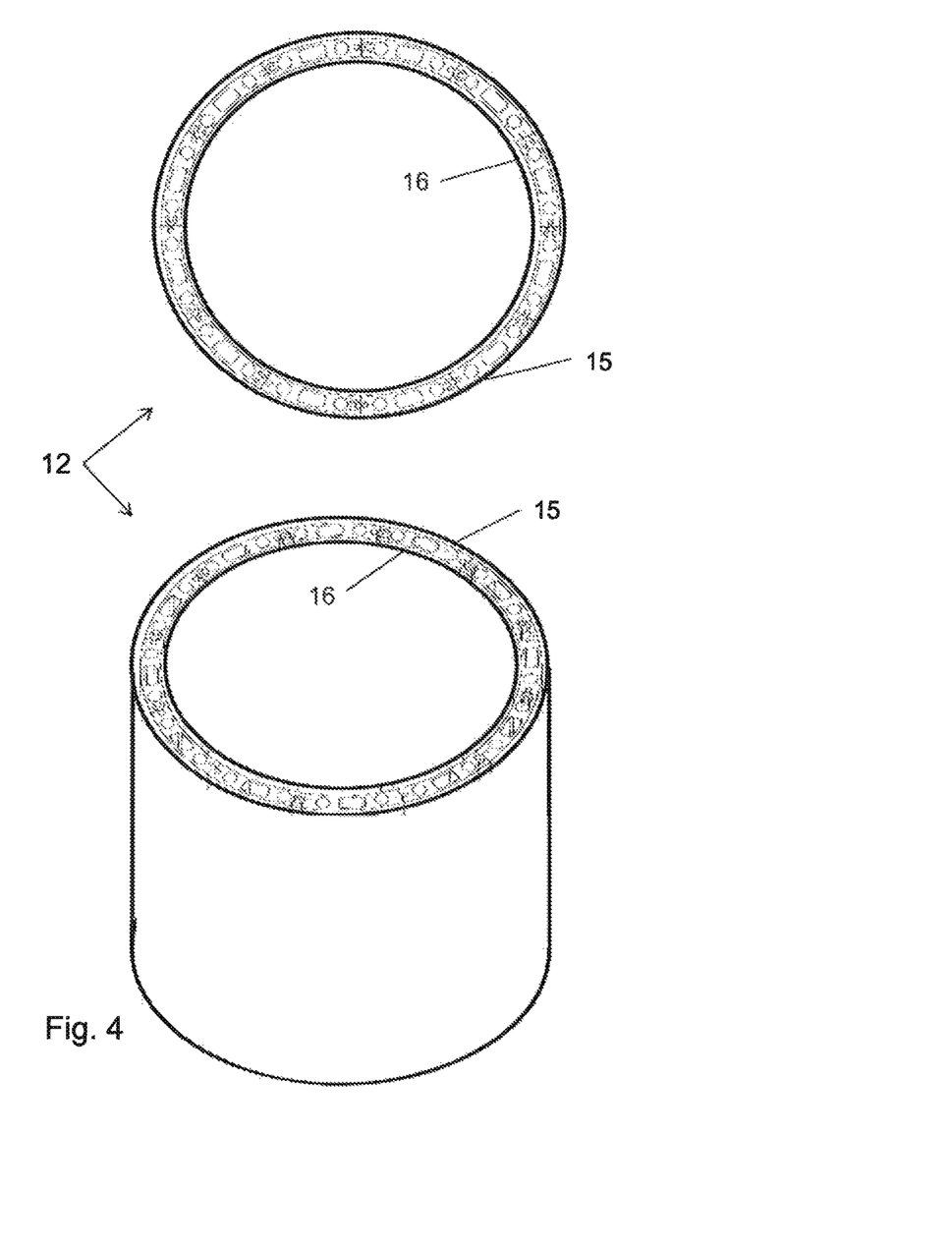
FIG. 4 shows the side wall of FIG. 3 with additional internal and external covers.
Figure 5:
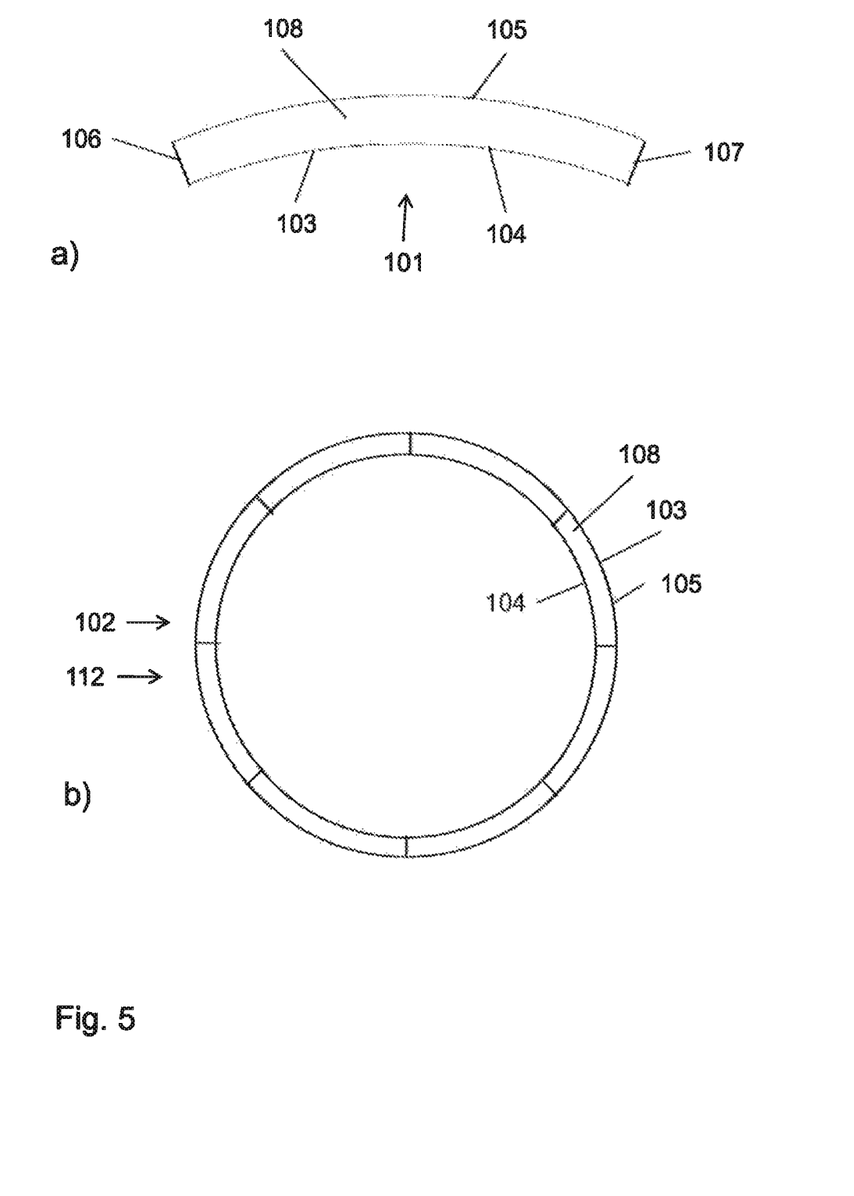
FIG. 5 shows a) an alternative hollow profile segment and b) a rigid cylindrical vessel side wall made up of these segments.

In some embodiments, illustrated by FIG. 2, one of the wide sides 4 comprises a baffle 17 protruding from the wide side 4 (the concave side if the segment is arc-formed). The baffle may e.g. have a triangular cross section. The baffle can also comprise a longitudinal baffle heat exchange channel 14, or a heat exchange channel 8 may also extend through the baffle as well as through the main body of the segment. This provides good heat exchange also via the baffle.

Figure 10:
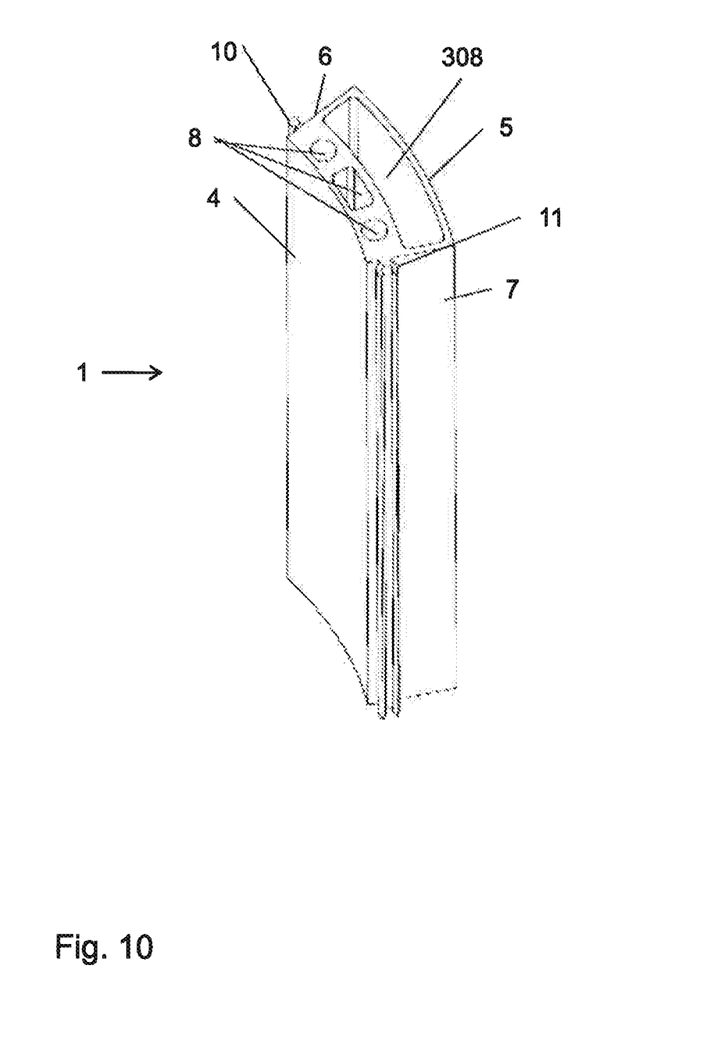
FIG. 10 shows a hollow profile segment (module) of the invention with an additional insulation channel.
Figure 11:
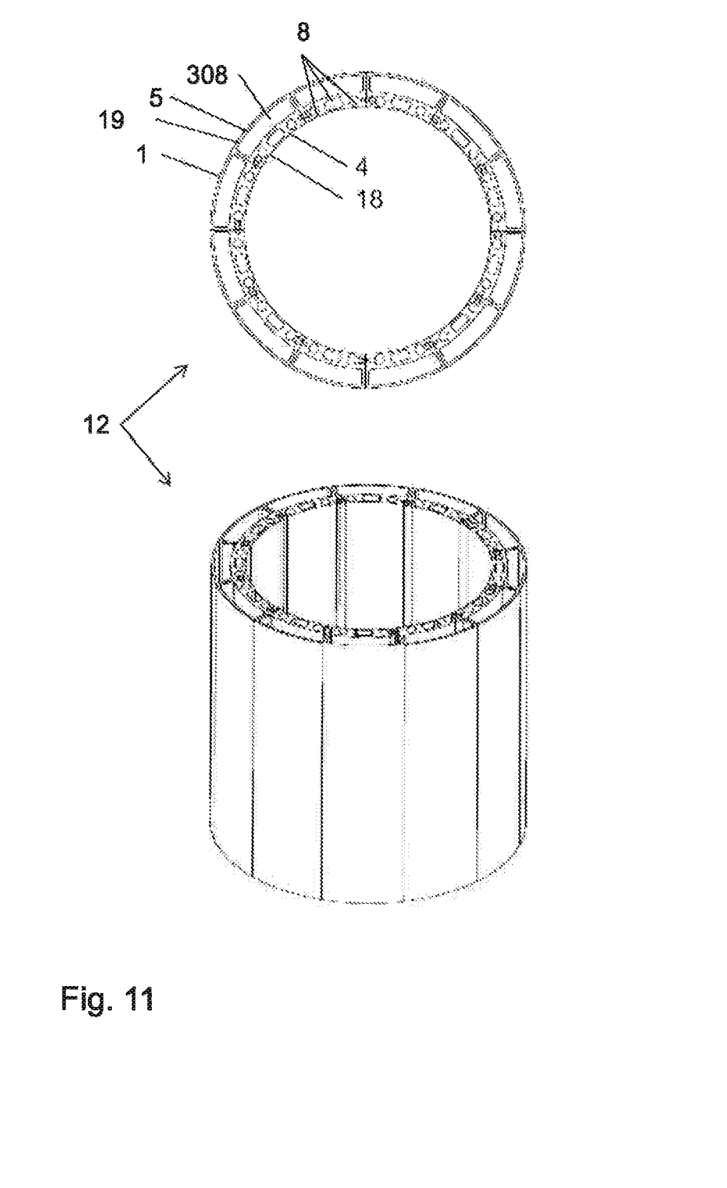
FIG. 11 shows a side wall of the invention with additional insulation channels in the hollow profile segments (modules).

In certain embodiments, illustrated by FIGS. 10 and 11, the hollow wall profile segment 1 comprises one or more additional insulation channels 308. The insulation channel(s) can suitably be located adjacent to one 5 of the wide sides, such as the convex side 5 if the segment has a circular arc cross section. The insulation channel(s) can then be located adjacent the outside 19 of a side wall composed of a plurality of profile segments, while the heat exchange channel(s) 8 for heat exchange fluid can be located near the inside 18 of the wall. This arrangement provides good temperature control and good external insulation. The insulation channel(s) may be filled with a thermal insulation material, such as e.g. a foam (e.g. polyurethane foam) or a fibrous material (e.g. glass wool or mineral wool). The profile segment may have a single insulation channel as shown in FIG. 10, but it may also have a plurality of insulation channels, suitably distributed along the (outer) wide side 5. The latter arrangement may provide higher mechanical stability due to the presence of internal walls between the insulation channels.

In a second aspect, illustrated by FIGS. 3-6, the invention discloses a side wall 12;112 of a bioreactor or mixer support vessel 2;2a;2b;102, which comprises a plurality of laterally joined hollow profile wall segments 1;101. The segments, e.g. each segment, comprises a base profile 3;103 with two parallel wide sides 4,5;104,105, two narrow sides 6,7;106,107 and at least one heat exchange channel 8;108 that extends in a longitudinal direction of the base profile through an interior space 9;109 in the base profile. As above, the length ratio W/N of the wide sides to the narrow sides may e.g. be at least about 5, such as at least about 10, and/or the ratio of the segment length L to the wide side length W may e.g. be at least about 5, such as at least about 10. The base profile may also have a substantially constant cross section geometry along a longitudinal axis 13, e.g. over at least 80% or at least 90% of the length of the profile or over the entire length of the profile. The wall segments are joined side by side to form the side wall, e.g. via the coupling members. The joints can suitably be capable of withstanding the hydrostatic pressure from a liquid-filled flexible bag on the inside of the side wall. The wall segments can be as discussed in the embodiments above but they can also have other types of geometries. For example, they can be tubes 103 with rectangular or arc-shaped cross section, a hollow interior (heat exchange channel) 108 and a tube wall composed of two parallel wide sides 104,105 and two narrow sides 106,107. The tubes 103 may be joined side by side, e.g. by welding or soldering the respective narrow sides to each other. The side wall can be cylindrical, e.g. circular cylindrical (i.e. with an essentially circular cross section), or alternatively it can have a polygonal prism shape (i.e. having a polygonal cross section). It can further comprise an external cover 15, which may e.g. comprise a thermal insulation layer. Alternatively, or additionally, the side wall can also comprise an internal cover 16, comprising e.g. a sheet-formed material such as a metal sheet, e.g. of stainless steel, or a plastic sheet. If a metal sheet comprising a different metal than the wall segments is used, a non-metallic protective layer or extra sheet may be provided to prevent the formation of galvanic elements. The internal cover can provide a smooth surface for contacting a flexible bag and it may also provide corrosion protection for the wall segments in case of bag leakage. In addition to, or as an alternative to the internal cover, the side wall may comprise a plurality of internal seal strips covering the coupling members to provide a smooth surface. It is also possible to apply one or more support rings (hoops) on the outside 19 or the external cover 15, to provide additional support against internal pressures.

In some embodiments, the side wall comprises a plurality of hollow profile wall segments each having a baffle 17 protruding from a wide side 4 on an inside 18 of the side wall and a plurality of hollow profile wall segments without baffles. The baffled segments can suitably be interspersed with non-baffle segments in such a way that the baffles are evenly distributed along the inside of the side wall. The side wall may e.g. comprise 2, 3, 4, 5 or 6 baffles. As discussed above, the baffles may contribute to the heat exchange via baffle heat exchange channels 14 or heat exchange channels 8 extending through the baffles.

Figure 6:
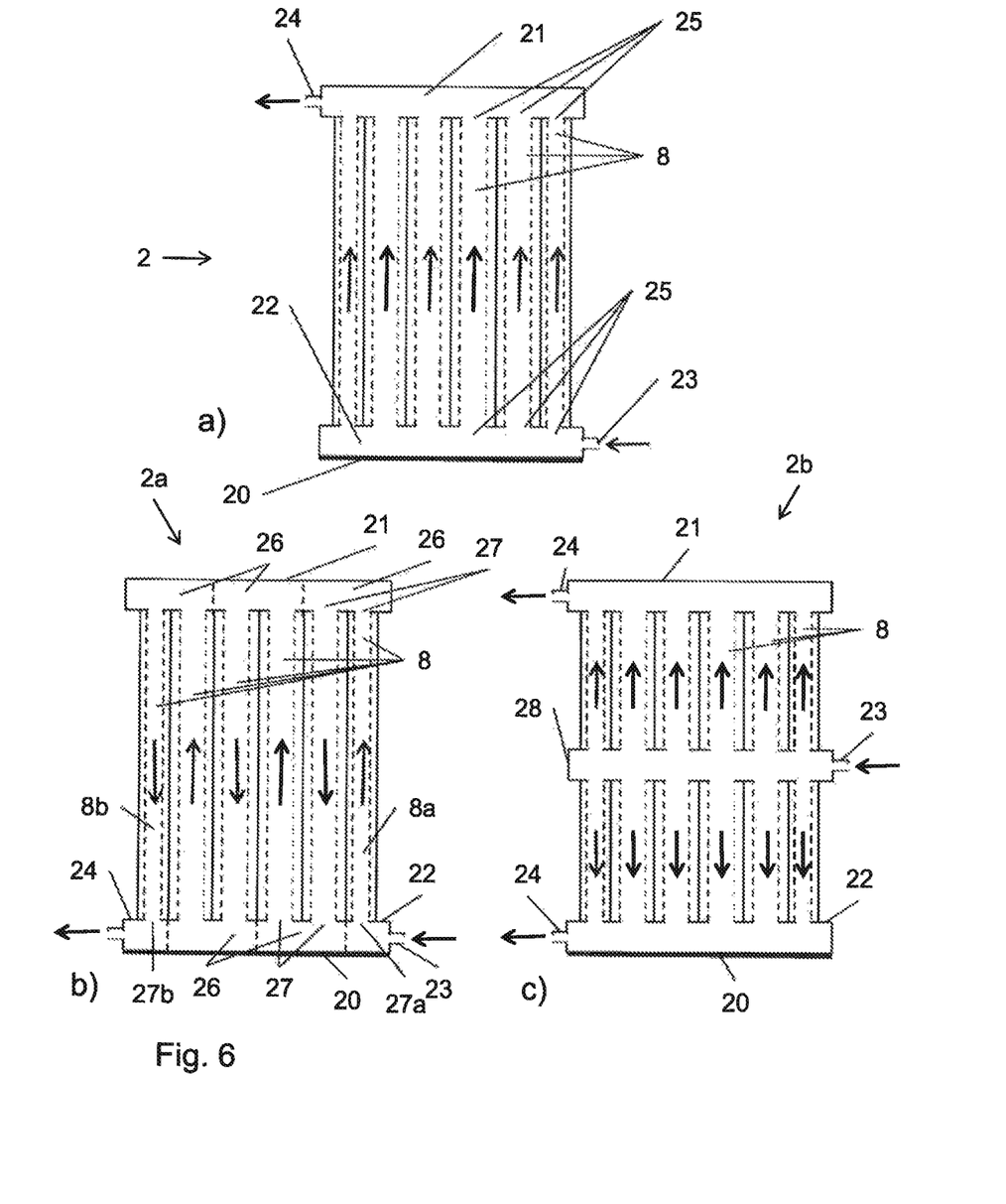
FIG. 6 shows cylindrical support vessels with axially aligned hollow profile segments that are connected to a top and bottom fluid manifold and to a bottom wall. a) parallel connection of heat exchange channels, b) serial connection of heat exchange channels, c) parallel connection with an intermediate manifold.

In a third aspect, illustrated by FIGS. 6 a)-c), the invention discloses a bioreactor or mixer support vessel 2;2a;2b; 102, comprising the side wall 12;112 as discussed in the embodiments above. The inner volume of the vessel may e.g. be at least 25 1, such as 25-2000 1, 50-2000 1 or 50-1000 1. An advantageous concept to manage the distribution of HX fluid over the individual segments is to build a barrel like construction (for the example a cylindrical vessel) and to connect the hollow segments at top and bottom to a circular or annular structure that provides mechanical support and fixation, liquid connections and the fluid distribution features desired. The support vessel comprises a bottom wall 20 and top 21 and bottom 22 distribution manifolds, which may be annular, where the manifolds fluidically connect a plurality of the heat exchange channels 8 with an inlet 23 and an outlet 24. The manifolds 21,22, also called distribution manifolds, are used in order to guide the XII fluid, providing uniform efficiency over the jacketed area of the vessel. The area covered by individual segments is selected such that the temperature loss along the segment is optimal. The top and bottom distribution manifolds may suitably comprise an inlet 23 or outlet 24 fluidically connected to a plurality of heat exchange channel connector ports 25 in register with the heat exchange channels 8. This arrangement provides a parallel coupling of the heat exchange channels such that heat exchange fluid can pass from the inlet to the outlet via a parallel set of heat exchange channels. Alternatively, the top and bottom distribution manifolds may comprise an inlet 23 fluidically connected to a first heat exchange channel connector port 27a in register with a first heat exchange channel 8a and a plurality of heat exchange channel interconnector conduits 26, each of which is fluidically connected with two adjacent heat exchange channels 8 via heat exchange channel interconnector ports 27 in register with said two adjacent heat exchange channels. A last heat exchange channel 8b may then be fluidically connected via a last heat exchange channel connector port 27b to an outlet 24. This allows serial coupling of the heat exchange channels, such that the heat exchange fluid passes from the inlet through one heat exchange channel after another before reaching the outlet. In addition to the top and bottom manifolds, the support vessel 2b may also comprise one or more further manifolds 28, as illustrated by FIG. 6 c), where a third manifold 28 distributes heat exchange fluid from inlet 23 in both upwards and downwards directions via the heat exchange channels 8 to the outlets 24. It is also possible to arrange fluidic connection between heat exchange channels by lateral ports (not shown) in the wall segments. In this case, at least two adjacent hollow profile wall segments comprise lateral ports, fluidically connecting the heat exchange channels 8 of the segments with each other. This could for example be achieved by creating an opening perpendicular to the direction of extrusion (by drilling or cutting) and fitting a sealing to this opening. Multiple segments could then be joined through such adjacent openings and sealings, the segments could be clamped against each other like the staves of a barrel.

Figure 9:
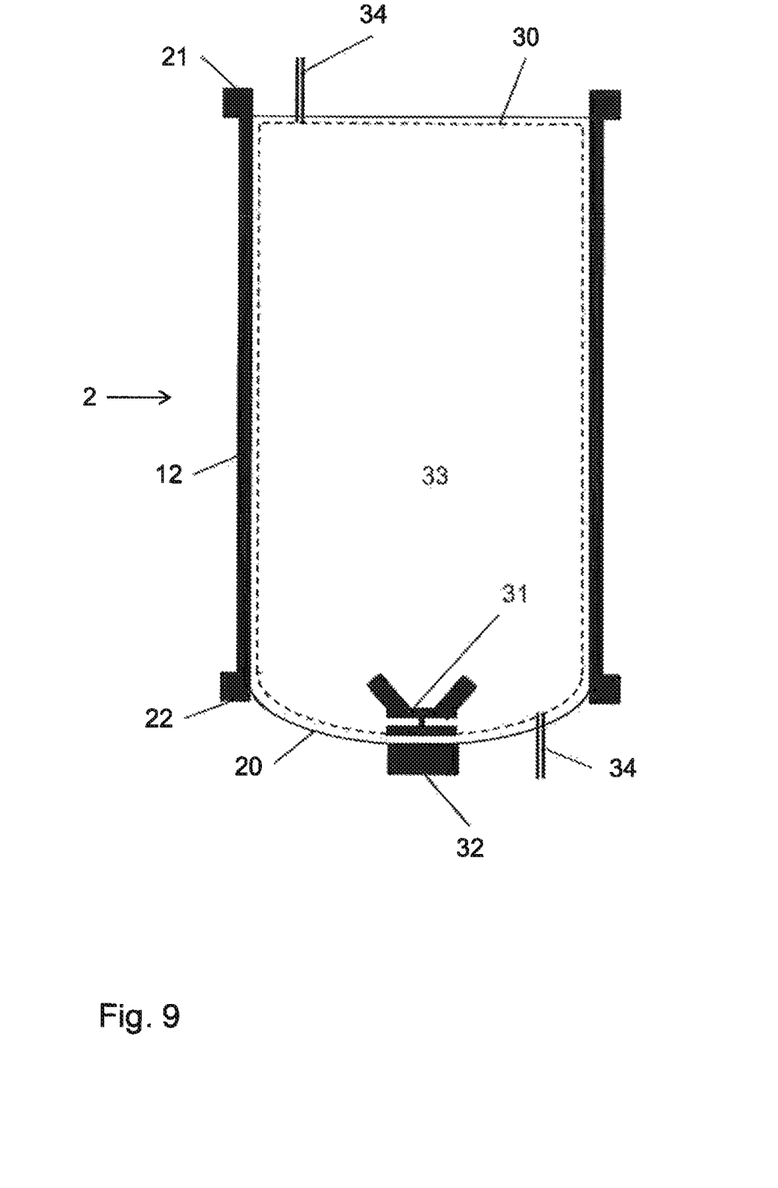
FIG. 9 shows a bioreactor/mixer of the invention, with a flexible bag mounted in a support vessel.

In a fourth aspect, illustrated by FIG. 9, the invention discloses a bioreactor or mixer comprising a flexible bag 30 mounted in the support vessel 2 as discussed in the embodiments above. The flexible bag may e.g. be manufactured from a plastic laminate and may e.g. be loaded into the vessel from the top of the vessel. In the interior volume of the bag 33, cells can be cultivated or process liquids, e.g. buffers can be mixed. Through one or more ports 34 in the bag, fluids can be added and removed as needed in the process. The bag may also comprise a magnetically driven impeller 31 for agitation, which may be driven by a magnetic drive unit 32 in or adjacent to the support vessel. The flexible bag may be supplied presterilized, e.g. by gamma irradiation and may be used a single-use item, obviating the need for cleaning and cleaning validation of reusable vessels. During operation of the bioreactor or mixer, inlet 23 and outlet 24 are suitably fluidically connected to a supply of HX fluid, such that HX fluid of suitable temperature is circulated through the manifolds 21,22,23;221,222 and the heat exchange channels 8,8a,14;208 to maintain the content of the flexible bag 30 (e.g. a cell culture or a process liquid) at a desired temperature. For cell culture, the desired temperature is often in the 30-40° C. range, but temperatures outside this range, e.g. 0-60° C., may also be used, particularly for mixers or for cultivation of thermophilic or psychrophilic organisms.

Figure 7:
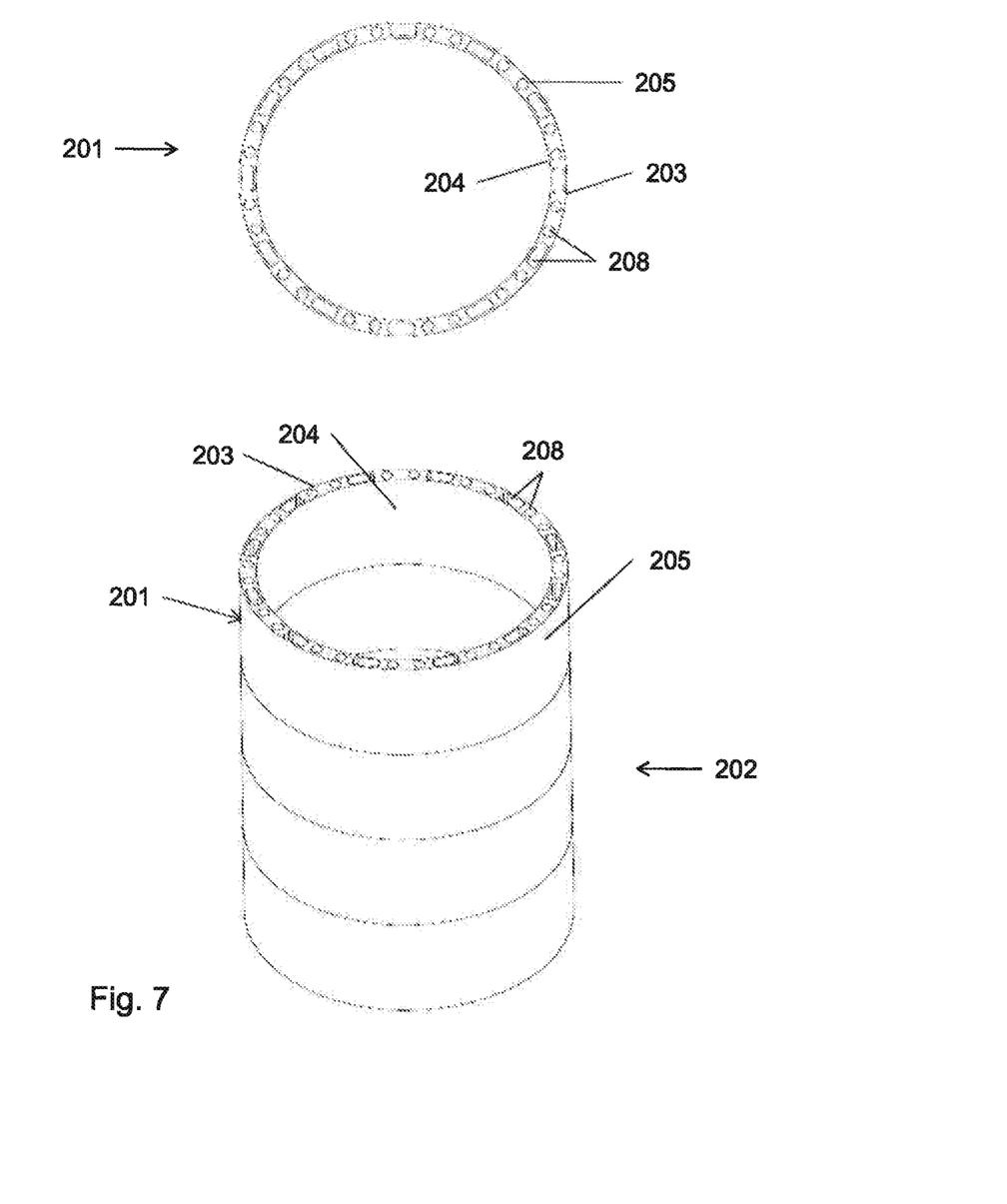
FIG. 7 shows extruded, ring shaped, elements stacked on top of each other to build a side wall for a cylindrical vessel. Rectangular or other geometries could be made accordingly. The fluid flow inside the elements can be mangaged both axially and laterally depending on the module configuration and the sealing and intermediate plates that could be stacked in between the extruded modules.
Figure 8:
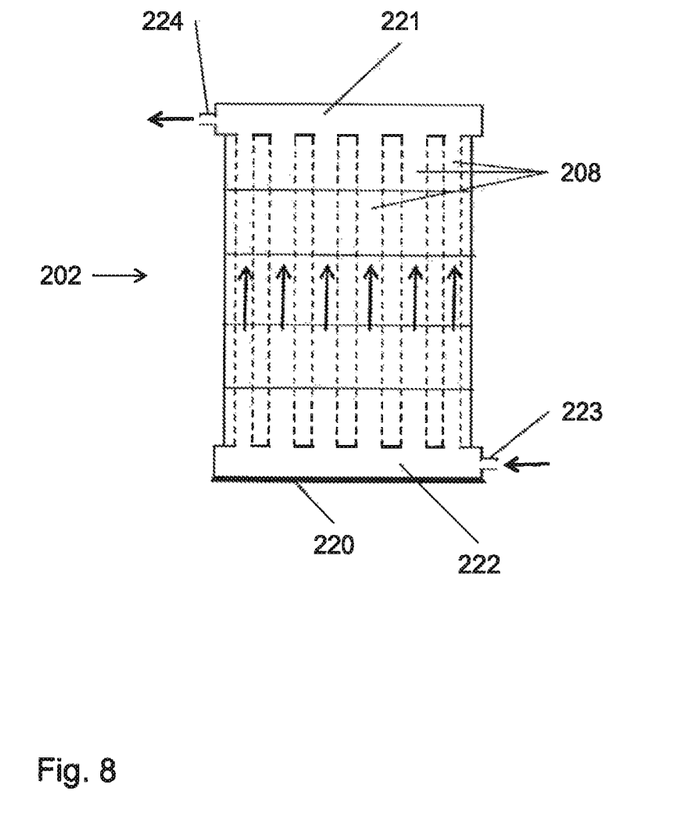
FIG. 8 shows a cylindrical vessel with the side wall of FIG. 7 and top and bottom manifolds and a bottom wall.

In a fifth aspect, illustrated by FIGS. 7-8, the invention discloses a hollow profile wall section 201 for a cylindrical bioreactor or mixer support vessel 202 side wall, which comprises a base tubular section 203 with an inner surface 204, an outer surface 205 and a plurality of heat exchange channels 208 extending in an axial direction through the base tubular section, wherein the hollow profile wall section is arranged to be stacked with similar hollow profile wall sections. The tubular sections could be annular, but they could also cover a larger or substantially the complete cylindrical surface to provide also a bottom structure of a vessel, for example. The tubular sections may be manufactured e.g. by extrusion, such as by extrusion of aluminium or an aluminium alloy.

in a sixth aspect, illustrated by FIGS. 7-8, the invention discloses a cylindrical side wall 202 of a bioreactor or mixer support vessel, comprising a plurality of stacked hollow profile wall sections as discussed in the embodiments above, wherein the heat exchange channels of the stacked sections are in register with each other.

In a seventh aspect, illustrated by FIG. 8, the invention discloses a bioreactor or mixer support vessel comprising a cylindrical side wall 202 as discussed in the embodiments above, a bottom wall 220 and top 221 and bottom 222 distribution manifolds, fluidically connecting a plurality of the heat exchange channels with an inlet 223 and an outlet 224. Although FIG. 8 shows a parallel flow arrangement, it is equally possible to obtain serial flow by an arrangement analog to FIG. 6 b). Further, a flexible bag may be mounted in the support vessel as illustrated in FIG. 9, to be used as a bioreactor or mixer as discussed above for the vessels having side walls made up of segments joined side by side.

In an eighth aspect, the invention discloses a method of cultivating cells in the bioreactors disclosed above. The method comprises the steps of:
 a) providing a bioreactor with a flexible bag as discussed above. The flexible hag can suitably be supplied presterilized.;
 b) adding cells and culture medium to the flexible bag, suitably under aseptic conditions.;
 c) cultivating cells in the flexible bag, suitably under agitation with addition and removal of gases (e.g. air and carbon dioxide) and under thermostated conditions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties as if individually incorporated.

The invention claimed is:

1. A modular hollow profile wall segment for a bioreactor or mixer support vessel, comprising a base profile with two parallel wide sides, two opposing narrow sides joining the two parallel wide sides, each of the two opposing narrow sides having at least one coupling member, at least one heat exchange channel extending in a longitudinal direction of said base profile through an interior space in said base profile between the two parallel wide sides and the two opposing narrow sides in a longitudinal path through one end of the interior space to an opposing end that is entirely direct and linear from the one end to the opposing end without curving, the at least one heat exchange channel configured to circulate a heat exchange fluid therethrough, wherein the at least one heat exchange channel comprises a plurality of individual heat exchange channels, each of the plurality of individual heat exchange channels spaced apart from an adjacent individual heat exchange channel, and an insulation channel extending in a longitudinal direction of said base profile through the interior space in said base profile between the two parallel wide sides and the two opposing narrow sides adjacent each of the plurality of individual heat exchange channels that form the at least one heat exchange channel, the insulation channel having a thermal insulation material filled therein, wherein the insulation channel is separate and distinct from the at least one heat exchange channel, wherein said modular hollow profile wall segment is adapted to be joined with similar modular hollow profile wall segments side by side to form a side wall of the bioreactor or mixer support vessel.

2. The modular hollow profile wall segment of claim 1, wherein said base profile has a substantially constant cross section geometry along a longitudinal axis, wherein the substantially constant cross section geometry extends over at least 90% of the length of said base profile.

3. The modular hollow profile wall segment of claim 1, wherein said base profile is an extruded profile.

4. The modular hollow profile wall segment of claim 3, wherein said base profile is an extruded aluminum or aluminum alloy profile.

5. The modular hollow profile wall segment of claim 1, wherein said at least one heat exchange channel contains one or more internal baffle elements.

6. The modular hollow profile wall segment of claim 1, wherein a first narrow side comprises a male coupling member and a second narrow side comprises a female coupling member.

7. The modular hollow profile wall segment of claim 1, wherein said two opposing narrow sides each comprises a genderless coupling member.

8. The modular hollow profile wall segment of claim 1, wherein said at least one coupling member comprises a recess, a track or a protrusion.

9. The modular hollow profile wall segment of claim 1, wherein one of said two parallel wide sides comprises a baffle protruding from one of said wide sides.

10. The modular hollow profile wall segment of claim 9, wherein said baffle has a triangular cross section.

11. The modular hollow profile wall segment of claim 1, generally shaped as a sector of a circular tubular cylinder.

12. The modular hollow profile wall segment of claim 1, which is generally rectangular.

13. A side wall of a bioreactor or mixer support vessel, comprising: a plurality of modular hollow profile wall segments joined side by side, each modular hollow profile wall segment comprising a base profile with two parallel wide sides, two opposing narrow sides joining the two parallel wide sides, at least one heat exchange channel extending in a longitudinal direction of said base profile through an interior space in said base profile between the two parallel wide sides and the two opposing narrow sides in a longitudinal path through one end of the interior space to an opposing end that is entirely direct and linear from the one end to the opposing end without curving, the at least one heat exchange channel configured to circulate a heat exchange fluid therethrough, wherein the at least one heat exchange channel comprises a plurality of individual heat exchange channels, each of the plurality of individual heat exchange channels spaced apart from an adjacent individual heat exchange channel, and an insulation channel extending in a longitudinal direction of said base profile through the interior space in said base profile between the two parallel wide sides and the two opposing narrow sides adjacent each of the plurality of individual heat exchange channels that form the at least one heat exchange channel, the insulation channel having a thermal insulation material filled therein, wherein the insulation channel is separate and distinct from the at least one heat exchange channel.

14. The side wall of claim 13 which is cylindrical.

15. The side wall of claim 13, further comprising an external layer.

16. The side wall of claim 13, further comprising an internal layer.

17. The side wall of claim 13, wherein each of the two opposing narrow sides of each modular hollow profile wall segment comprises a coupling member, each coupling member configured to couple with a coupling member of an adjacent modular hollow profile wall segment, wherein one coupling member comprises a protrusion member extending outward from one of the narrow sides and stretching a full length of that side, and a second coupling member comprises an open channel extending outward from the other of the narrow sides and stretching a full length of that side, the one coupling member and the second coupling member configured to mate complementary with an opposing coupling member of the adjacent modular hollow profile wall segment.

18. The side wall of claim 13, wherein the plurality of modular hollow profile wall segments comprise a mix of modular hollow profile wall segments having a baffle protruding from an inner wall on a wide side towards an interior of the bioreactor or mixer support vessel and modular hollow profile wall segments without the baffle protruding from an inner wall on a wide side towards the interior of the bioreactor or mixer support vessel.

19. The side wall of claim 13, wherein the sidewall is generally shaped as a sector of either a circular tube or polygonal prism.

20. The side wall of claim 18, wherein the baffle comprises a baffle body that protrudes from the inner wall on the wide side towards the interior of the bioreactor or mixer support vessel and a heat exchange baffle channel extending in a longitudinal direction through an interior space in the baffle body, wherein the heat exchange baffle channel is surrounded completely by the interior space of the baffle body.

21. The side wall of claim 13, wherein a first of the two parallel wide sides forms an inner wall of the bioreactor or mixer support vessel and a second of the two parallel wide sides forms an outer wall of the bioreactor or mixer support vessel, wherein the at least one heat exchange channel abuts the inner wall of the bioreactor or mixer support vessel and the insulation channel with the thermal insulation material fill therein abuts the outer wall of the bioreactor or mixer support vessel.

22. The side wall of claim 13, wherein each of the plurality of individual heat exchange channels are separated by a material that is separate and distinct from the thermal insulation material filling the insulation channel.

23. The side wall of claim 13, further comprising a baffle protruding from an inner wall on a wide side towards an interior of the bioreactor or mixer support vessel, wherein the baffle comprises a heat exchange baffle channel extending in a longitudinal direction through an interior space in the baffle, wherein the heat exchange baffle channel is separate and distinct from the plurality of individual heat exchange channels.

24. A bioreactor or mixer support vessel comprising the side wall of claim 13, a bottom wall and top and bottom distribution manifolds, fluidically connecting a plurality of said heat exchange channels with an inlet and at least one outlet.

25. The support vessel of claim 24, wherein said top and bottom distribution manifolds are annular.

26. The support vessel of claim 24, wherein said top and bottom distribution manifolds comprise an inlet or outlet fluidically connected to a plurality of heat exchange channel connector ports in register with said heat exchange channels.

27. The support vessel of claim 24, wherein said top and bottom distribution manifolds comprise an inlet or outlet fluidically connected to a first heat exchange channel connector port in register with a first heat exchange channel and a plurality of heat exchange channel interconnector conduits, each fluidically connected with two adjacent heat exchange channels via heat exchange channel interconnector ports.

28. The support vessel of claim 24, further comprising a third distribution manifold, fluidically connecting a plurality of said heat exchange channels with an inlet or an outlet.

29. The support vessel of claim 24, wherein at least two adjacent hollow profile wall segments comprise lateral ports, fluidically connecting the heat exchange channels of said segments with each other.

30. A modular hollow profile wall section for a cylindrical bioreactor or mixer support vessel, comprising a base tubular section with an inner surface, an outer surface, a plurality of spaced heat exchange channels extending in a longitudinal direction through said base tubular section between the inner surface and the outer surface in a longitudinal path through one end of an interior space of the base tubular section to an opposing end that is entirely direct and linear from the one end to the opposing end without curving, each of the plurality of heat exchange channels configured to circulate a heat exchange fluid therethrough, and an insulation channel extending in the longitudinal direction of the base tubular section through the interior space thereof between the inner surface and the outer surface adjacent each of the plurality of heat exchange channels, the insulation channel having a thermal insulation material filled therein, wherein the insulation channel is separate and distinct from the plurality of heat exchange channels, wherein said modular hollow profile wall section is arranged to be stacked with similar modular hollow profile wall sections to form a side wall of the cylindrical bioreactor or mixer support vessel.

31. The modular hollow profile wall section of claim 30, wherein said base tubular section is an extruded aluminum or aluminum alloy section.

32. A side wall of a bioreactor or mixer support vessel, comprising:
a plurality of modular hollow profile wall segments,
each modular hollow profile wall segment further comprising a base profile with two parallel wide sides, two opposing narrow sides joining the two parallel wide sides, each of the two opposing narrow sides having a coupling member and at least one heat exchange channel extending in a longitudinal direction of said base profile through an interior space in said base profile between the two parallel wide sides and the two opposing narrow sides in a longitudinal path through one end of the interior space to an opposing end that is entirely direct and linear from the one end to the opposing end without curving, the at least one heat exchange channel configured to circulate a heat exchange fluid therethrough, wherein the at least one heat exchange channel comprises a plurality of individual heat exchange channels, each of the plurality of individual heat exchange channels spaced apart from an adjacent individual heat exchange channel, and an insulation channel extending in a longitudinal direction of said base profile through the interior space in said base profile between the two parallel wide sides and the two opposing narrow sides adjacent each of the plurality of individual heat exchange channels that form the at least one heat exchange channel, the insulation channel having a thermal insulation material filled therein, wherein the insulation channel is separate and distinct from the at least one heat exchange channel; said plurality of modular hollow profile wall segments joined side by side via corresponding coupling members to form a side wall of circular or polygonal cross section.

* * * * *